(12) United States Patent
Hoeffner

(10) Patent No.: US 10,260,948 B2
(45) Date of Patent: Apr. 16, 2019

(54) METHOD AND DEVICE FOR DETERMINING AND CALCULATING A SCATTERED RADIATION SPECTRUM AND METHOD FOR COMPRESSING DATA

(71) Applicant: LEIBNIZ-INSTITUT FÜR ATMOSPHÄRENPHYSIK E.V. AN DER UNIVERSITÄT ROSTOCK, Kühlungsborn (DE)

(72) Inventor: Josef Hoeffner, Kuehlungsborn (DE)

(73) Assignee: LEIBNIZ-INSTITUT FUER ATMOSPHAERENPHYSIK E.V. AN DER UNIVERSITAET ROSTOCK, Kuehlungsborn (DE)

( * ) Notice: Subject to any disclaimer, the term of this patent is extended or adjusted under 35 U.S.C. 154(b) by 423 days.

(21) Appl. No.: 14/648,010

(22) PCT Filed: Nov. 26, 2013

(86) PCT No.: PCT/EP2013/074781
§ 371 (c)(1),
(2) Date: Jul. 30, 2015

(87) PCT Pub. No.: WO2014/083014
PCT Pub. Date: Jun. 5, 2014

(65) Prior Publication Data
US 2015/0323386 A1 Nov. 12, 2015

(30) Foreign Application Priority Data
Nov. 29, 2012 (DE) .................... 10 2012 221 862

(51) Int. Cl.
*G01J 3/44* (2006.01)
*G01J 3/10* (2006.01)
(Continued)

(52) U.S. Cl.
CPC ............... *G01J 3/4412* (2013.01); *G01J 3/10* (2013.01); *G01N 21/538* (2013.01); *G01S 7/484* (2013.01);
(Continued)

(58) Field of Classification Search
CPC ........ G01J 3/4412; G01J 3/10; G01N 21/538; G01S 7/497; G01S 7/486; G01S 7/484; G01S 17/95; G01S 17/58
See application file for complete search history.

(56) References Cited

U.S. PATENT DOCUMENTS

| 6,459,093 B1 | 10/2002 | Dieckmann |
| 7,391,557 B1 | 6/2008 | Bruch et al. |
| 2008/0149838 A1 | 6/2008 | Parvin |

FOREIGN PATENT DOCUMENTS

| EP | 1416293 A1 | 5/2004 |
| WO | 2010124038 A2 | 10/2010 |

OTHER PUBLICATIONS

International Search Report dated May 19, 2014 in PCT/EP2013/074781.

*Primary Examiner* — Hwa Andrew Lee
(74) *Attorney, Agent, or Firm* — Fox Rothschild LLP

(57) ABSTRACT

The invention relates to a device (1) and a method (20) for determining a spectrum (X) of scattered radiation (S). The invention further relates to a method (70) for calculating the spectrum (X) and a method for compressing unstructured data (60) of known distribution. To be able to determine the spectrum (X) as precisely as possible and to derive from this the characteristics of materials that scatter laser pulses (P), the invention proposes that at least one characteristic of the laser pulse (P) is determined and that a spectrum analyzer (5) is used for this. Frequencies (F) of laser pulses (P) and volumes (M) of backscattered radiation (S) are combined into frequency and volume values (F', M') to calculate the (Continued)

Figure 1:
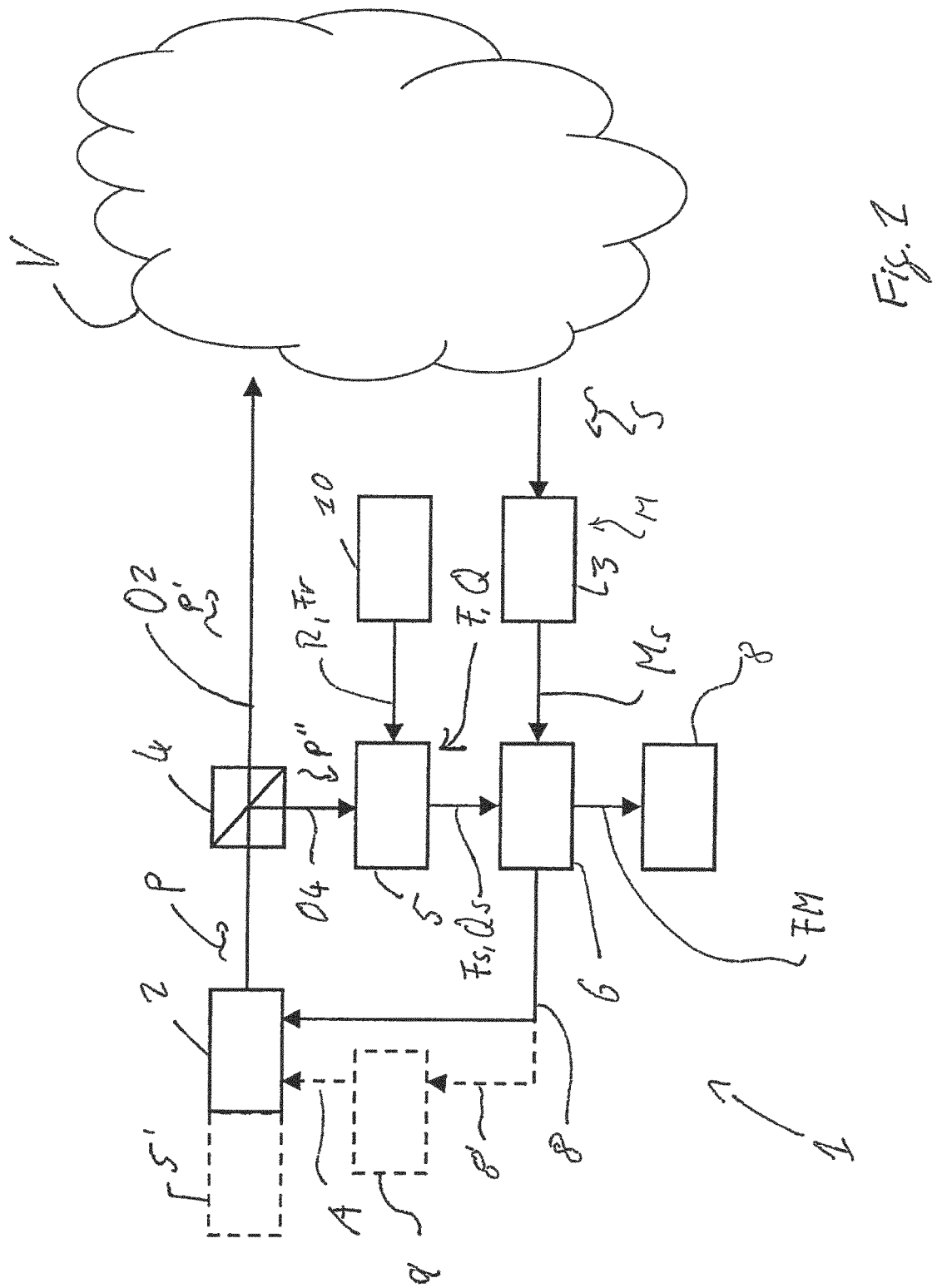

spectrum (X). The most frequent data values are deleted from the data to compress the data (60).

14 Claims, 5 Drawing Sheets

(51) Int. Cl.
| | | |
|---|---|---|
| | *G01S 17/95* | (2006.01) |
| | *G01S 7/484* | (2006.01) |
| | *G01S 7/486* | (2006.01) |
| | *G01S 7/497* | (2006.01) |
| | *G01N 21/53* | (2006.01) |
| | G01S 17/58 | (2006.01) |

(52) U.S. Cl.
CPC .............. *G01S 7/486* (2013.01); *G01S 7/497* (2013.01); *G01S 17/95* (2013.01); G01S 17/58 (2013.01)

METHOD AND DEVICE FOR DETERMINING AND CALCULATING A SCATTERED RADIATION SPECTRUM AND METHOD FOR COMPRESSING DATA

CROSS-REFERENCE TO RELATED APPLICATIONS

This application is a § 371 U.S. National Stage Entry of International Application No. PCT/EP2013/074781 filed Nov. 26, 2013, which claims priority to and the benefit of German Application No. 10 2012 221 862.9, filed Nov. 29, 2012, the entireties of both are hereby incorporated herein by reference.

The invention relates to a method for determining a spectrum of scattered radiation, wherein several laser pulses are successively scattered and the scattered radiations are measured, wherein at least one characteristic of the laser pulses is determined and associated with the scattered radiation for determining the spectrum. Furthermore, the invention relates to a device for determining a spectrum of scattered radiation, with a pulsed laser, whose laser pulses that are emitted during the operation of the device are scattered so as to generate the scattered radiation, and with a radiation sensor which is configured to at least partially receive the scattered radiation. The invention also relates to a method for calculating a scattered radiation spectrum. Moreover, the invention relates to a method for compressing unstructured data having a known distribution.

Methods and devices for determining scattered radiation spectra are generally known and are used to determine, for example, properties of matter. In particular, the laser pulses may be scattered by a gas to determine properties of the gas. The gas to be examined is frequently part of the atmosphere, whose properties are to be determined. The device is, for example, part of a so-called Lidar, which operates like radar, but uses laser radiation instead of radio waves. Conventional complex Lidar systems are able to determine concentrations of atmospheric trace gases, for example, to monitor emission levels of power plants.

The properties of the gas can hereby be determined the more accurately, the more accurately the spectrum of the scattered radiation is determined. A prerequisite for being able to determine the scattered radiation spectrum is, however, to keep the characteristics of the emitted laser pulses as stable as possible. However, the characteristics of individual laser pulses emitted by the pulsed laser vary unpredictably in conventional pulsed lasers to such an extent that many measurements cannot be carried out with sufficient precision. Stabilizing the characteristics of the laser pulses is already very complicated in the laboratory.

However, when the process is to be performed outside the laboratory, for example, on a ship or a satellite, the characteristics of some laser pulses may easily differ profoundly from the characteristics of other laser pulses or from a desired characteristic. For example, vibrations or sound causes a change in the optical path length of a resonator of the laser, which causes characteristics and, for example, the wavelength of the laser pulse to vary greatly from pulse to pulse. A control of the pulsed laser is impossible due to the short pulse length of the laser pulses of a few nanoseconds.

It is therefore the object of the invention to provide a method and a device for determining scattered radiation spectra of the aforementioned type, wherein scattered radiation spectra can be determined with the method and device with better measurement accuracy than before.

This object is attained for the aforementioned method by determining the frequency of the laser pulses as the characteristic. This object is attained for the aforementioned device by using a spectrum analyzer which is coupled to the pulsed laser for receiving the laser radiation and which is configured to determine a characteristic of the laser pulses.

Instead of attempting to build a pulsed laser at great expense whose laser pulses all have a very constant and preferably an exactly predetermined frequency, it is therefore sufficient to use conventional pulsed lasers having frequencies that may vary uncontrollably from pulse to pulse at least within certain limits. The characteristic of the laser pulse and in particular its frequency can be determined at least relatively with the spectrum analyzer, and can be stored in combination with measurement data generated by the radiation sensor. The scattered radiation spectrum can be accurately reconstructed from the combined data, even though the characteristics of the used laser pulses were neither stable nor known in advance. The progression of the measurement can be reconstructed from the data in a subsequent data analysis and the scattered radiation spectrum to be measured can be determined with significantly higher accuracy than would normally be possible considering the stability of the pulsed laser.

Due to the high accuracy, Doppler effects (Doppler broadening or Doppler shift) and, for example, the concentration of elements in a gas or other minimal changes known in spectroscopy, e.g. pressure changes, can be measured. In all cases, minimal changes of a spectrum, e.g. a line shape or a line width, should be detected with an accuracy that can generally be achieved only in high-precision laboratory measurements.

The frequency of the laser pulses may therefore be determined as the characteristic. Frequency measurements are comparatively easily and accurately performed. The wavelength of the laser pulses can readily be inferred from their frequency. The frequency of one of the laser pulses may be a distinguished frequency in its spectrum. In particular, the spectrum may have at the distinguished frequency its maximum or its center of gravity, wherein the center of gravity is preferred because it is more robust than the maximum. The measured frequencies of the laser pulses to be scattered are thus available for determining the scattered radiation spectrum.

Because the frequency is easy to measure, the scattered radiation spectra can be determined with the method and the device of the present invention with sufficient accuracy so that even the temperature or the wind speed of a gas in the atmosphere can be determined. For example, the laser pulses are directed into the atmosphere and scattered radiation of the laser pulses that is at least partially backscattered by the atmosphere to the device is received. The spectrum of the scattered radiation is, for example in a temperature measurement, Doppler-broadened compared to the frequency spectrum of the employed laser pulses. Such Doppler measurements require a precision of better than 1 MHz (wavelength accuracy of about 1 fm) for determining the temperature to about 1 Kelvin and the wind speed to 1 m/s. A change of the temperature corresponds to a change in line width of typically 1:500 or less.

For example, the detection of tides in the atmosphere based on resonance scattering requires an even higher accuracy. In this case, the amplitude of vertical tidal wind in the atmosphere is only about 0.1 m/s on average. Amplitudes in a speed range of cm/s and less must be determined when measuring the Doppler shift due to aerosols in the middle stratosphere. The instrument must therefore be able to repeatedly measure spectra for very long periods of time with an accuracy of ~10 kHz in the frequency determination.

Even such low wind speeds can be measured with the method and device of the present invention. The device is capable of repeatedly determining scattered radiation spectra with an accuracy of up to 10 kHz or better for very long periods of time, e.g. several hours, days or weeks. The accuracy achieved in the measurement frequency of each laser pulse is about a factor of about $10^{-10}$ of the frequency of the emitted laser pulses and is thus significantly better than 1 MHz for each laser pulse used to determine the scattered radiation spectrum.

The inventive solution can be further improved by various embodiments that have separate advantages and can be combined in any configuration. These embodiments and their associated benefits will be discussed below.

In a first advantageous embodiment, at least a portion of the scattered radiation may be detected for each laser pulse and the quantity of the detected scattered radiation of the scattered laser pulse may be linked with the determined characteristic, i.e. the frequency of the laser pulse. For example, the radiation sensor is configured to receive a portion of the scattered radiation and to generate a measurement or quantity signal that is dependent on the quantity of the received scattered radiation.

Especially when determining properties of the upper atmosphere, for example the mesosphere, the amount of receivable scattered radiation is very low. Often, not even one scattered photon per laser pulse is received. The amount of detected scattered radiation can be the number of photons scattered and received for each laser pulse. Alternatively, the amount may correspond to the intensity of the detected scattered radiation per laser pulse.

Especially when using the device outside the laboratory, for example vibrations may cause at least some of the laser pulses to be unsuitable for determining the gas properties. Already a few unsuitable laser pulses can appreciably worsen the accuracy of the scattered radiation spectrum. In order to be able to determine the scattered radiation spectrum even when carrying out the method or using the device outside of a stable laboratory, a quality feature for the laser pulses may be determined. Only those laser pulses and the scattered radiation associated therewith, whose quality feature satisfies a quality criterion, are used to determine the scattered radiation spectrum.

For example, multimode laser pulses or broadband emissions from the pulsed laser having a frequency range of more than e.g. 1000 GHz do not satisfy the quality criterion. Even if the laser pulse exhibits such complications less than one percent of the time, the measured spectrum of scattered radiation is greatly distorted in such a way that the measurement quality noticeably deteriorates. Defective laser pulses can be identified by determining, for example, their laser spectrum and by then determining the quality feature based on this laser spectrum. The laser spectrum can also be used to determine the frequency of the laser pulses. A separate measurement of the frequency is thus not required and the quality feature and the frequency of the laser pulse can be determined in a single step.

With the method according to the invention it is therefore first ensured that the laser pulse satisfies the quality criterion. If the laser pulse does not meet the quality criterion, then its frequency and the scattered radiation caused by the laser pulse is not used to determine the scattered radiation spectrum and the gas property. Only good laser pulses meeting the quality criterion are used for the determination, and their specific characteristic, in particular their frequency, is linked with the amount of scattered radiation associated with the laser pulse.

To be able to determine at least the characteristic and in particular the frequency and possibly also the quality feature of the laser pulses, the spectrum analyzer may include an interferometer that superimposes incident laser light on itself, a measurement signal converter and a lens, wherein the lens is disposed between the interferometer and the measurement signal converter in a beam path of laser light emitted from the interferometer and propagating to the measurement signal converter.

The lens is preferably a convex lens, which images the interference pattern of the laser radiation that is theoretically formed only at infinity on the measurement signal converter, for example, a one- or two-dimensional sensor, such as a line camera or an area scan camera. In this way, spectra can be determined over virtually any frequency range. In particular, by using a two-dimensional sensor, other characteristics in addition to the frequency can be easily identified, for example broadband emission from the pulsed laser. Undesirable modes of the laser pulses can also be determined with a one-dimensional sensor when using a high-resolution interferometer.

The interferometer is preferably a Fabry-Perot etalon and is, for example, arranged directly on the pulsed laser, so that a portion of each of the laser pulses in the interferometer is superimposed on itself and outputted through the lens to the measurement signal converter. With the interferometer, the spectrum analyzer can be used unchanged over a very wide wavelength range of up to several hundred nanometers. With a sufficiently large Fabry-Perot interferometer, all necessary quantities for the frequency determination can be determined from the interference pattern itself when imaging over at least two free spectral ranges (2 rings). The only required dimension for an accurate determination of a frequency shift is the distance between the two mirrors, which can be determined directly with extremely high precision during the construction. Alternatively, the mirror spacing can be determined later by using the reference laser, if a sufficient number and in particular at least two accurately known wavelengths are available.

If the distance between two frequencies is greater than a free spectral range of the interferometer, then the frequencies cannot be uniquely determined with the spectrum analyzer. If the free spectral range is for example 1000 MHz, then the spectrum analyzer generates, for incident laser radiation with relative frequencies of, for example, 300 MHz, 1300 MHz and 2300 MHz, essentially identical measurement data or ring images that do not allow a conclusion as to whether the frequency of the laser radiation is now 300 MHz, 1300 MHz or 2300 MHz. Only frequency differences that are less than the free spectral range, in the present example less than 1000 MHz, can be unambiguously identified.

In order to be able to at least relatively determine frequencies with a mutual separation from one another that is greater than the free spectral range of the interferometer, the frequency of the laser radiation and in particular of the individual laser pulses can at least initially be determined very coarsely and in particular with an accuracy that is better than the free spectral range. When the relative frequency is coarsely determined, it can thereafter be exactly determined inside the free spectral range by using the spectrum analyzer.

For a coarse determination of the frequency of the laser pulses, characteristics such as operating parameters of the pulsed laser or of a seeder laser exciting the pulsed laser can be used. The frequency of the laser pulses can, for example, depend from an electric operating current and/or an electric operating voltage of the pulsed laser or the seeder laser. Other operating parameters of the laser, for example, the gas pressure of a gas laser, can also affect the frequency of the laser pulses and can therefore be used for a coarse determination of the frequency.

Preferably, the relative frequency of the laser pulse is hence initially determined coarsely and in particular with an accuracy within the free spectral range of the interferometer based on an operating parameter of a laser involved in the generation of the laser pulse, with the exact relative frequency then being determined based on the coarsely determined relative frequency through a measurement with the spectrum analyzer.

In particular, the distance between the two mirrors of the interferometer may be unchangeable, so that the interferometer can be mechanically constructed with extreme stability. The Fabry-Perot etalon can advantageously have almost any mirror spacing (high spectral resolution) and be a concentric ring system. Errors in the interferometer can be detected and averaged by detecting the entire ring system. In addition, the statistics per laser pulse is significantly improved. The accuracy of the spectrum analyzer is limited, inter alia, by the finite dynamics of the measuring sensor. By using the entire ring system, many identical measurements are virtually performed along many diameters of the ring system, thereby significantly increasing the accuracy. Mechanical changes, for example due to heating of the camera at the start of measurement, cause a change in the position of the interferogram on the measurement signal converter which can be calculated and taken into account. This significantly reduces the demand on the mechanical design of the spectrum analyzer.

With a mechanically stable interferometer, the Lidar system can be used in a mobile setting, i.e. on a ship or a motor vehicle, or can be designed for use in a space laboratory transported on a rocket, without change in the characteristics of the interferometer due to vibrations. However, if the characteristics of the interferometer nevertheless change, then these changes can often be detected by using the reference laser.

Due to its characteristics, the spectrum analyzer also enables an assessment of the broadband emission of the pulsed laser, which may extend over an extremely wide frequency range, for example, over more than 1,000 GHz, and which cannot be readily detected by other methods. The spectrum analyzer can be used unchanged as an interferometer over a very wide wavelength range of up to several hundred nanometers. Spectra can then be determined over a frequency range of virtually any size.

Frequencies of the laser pulses relative to an arbitrary frequency can be determined by using the aforedescribed device and the aforedescribed method. The arbitrary frequency forms an arbitrary zero (origin), which is determined by the stability of the spectrum analyzer. However, since the spectrum analyzer can change over time, for example due to a change in the ambient temperature, a relative determination of the frequency of the laser pulses may not be sufficient for repeatedly carrying out accurate measurements. In order to recognize and compensate for the changes of the spectrum analyzer, the device may include a reference frequency source, in particular in the form of a reference laser, for example a rubidium laser. The reference laser is preferably stabilized on the narrowest possible reference line, e.g. through saturation spectroscopy based on rubidium. The interferometer, the lens and the measurement signal converter may be arranged in the beam path of the reference frequency source. Radiation emitted from the reference frequency source has a well-known or at least a stable frequency.

The use of the reference laser obviates the need for using a frequency comb generator. The spectrum analyzer can be controlled so precisely with the reference laser that relative frequencies of the individual laser pulses can be measured with sufficient accuracy, even when the spectrum analyzer may have changed, for example due to temperature variations or vibrations.

To determine whether the spectrum has changed, the frequency of a reference laser beam emitted from the reference frequency source can determined before or after at least one of the laser pulses, and the frequency of the previous and/or the following laser pulse can be determined relative to the frequency of the reference laser beam. Even when the long-term frequency stability of the reference laser is not absolutely known, changes of the spectrum analyzer can be determined by random or repeated measurements of the frequency of the reference laser. If the frequency of the reference laser measured with the spectrum analyzer deviates too much from a desired reference frequency, e.g. from a previously measured frequency of the reference laser, then this deviation is evidence of an undesirable change in the spectrum analyzer. The deviation and in particular its magnitude may also be used for, for example, a mathematical correction of the particular frequency of the laser pulses. The mathematical correction may simply involve using the difference between the most recently determined reference frequency and the nominal reference frequency as an offset, wherein the offset is added to or subtracted from, for example, the measured frequency of the laser pulses as a correction. A mathematical correction of higher order can be used for an even greater accuracy of the correction when the reference frequency deviates from the frequency to be measured.

When using the reference laser, it is not necessary to use a long-term stable interferometer or a long-term stable etalon that does not change even in mechanically demanding environments, such as on an automobile. If the interferometer or etalon changes, for example as a result of vibrations, such changes can be detected and compensated for by measuring the reference frequency. For example, the device according to the invention can be launched with a rocket into space as part of a space laboratory, without the transport having a negative effect on the measurement accuracy of the device. The interferometer or etalon may hereby have a relatively simple and thus inexpensive or lightweight construction.

The device may also be operated without the reference laser. However, the measurement accuracy of the device then depends on the stability of the interferometer or etalon.

To be able to detect even short-term changes of the spectrum analyzer, the frequency of the reference laser beam may be determined with the spectrum analyzer between successive laser pulses and particularly between all laser pulses, and the frequency of the previous and/or the following laser pulse may be determined relative to the determined frequency of the reference laser beam.

The reference laser beam may be a continuous wave laser beam that is continuously generated and then used as a pulsed laser beam between the laser pulses for calibrating the spectrum analyzer. Knowledge of the absolute wavelength of the reference laser is not necessary, since the reference laser is used only for determining the change of the spectrum analyzer over time.

This process of comparing the pulsed laser and the reference laser in extremely short time intervals makes it possible to determine the frequency of the pulsed laser with about the same accuracy as the frequency of the reference laser. The reference laser may, for example, be a diode laser which is stabilized in relation to an Rb saturation spectroscopy. This method which is also applied in atomic clocks allows a frequency stability of $<10^{10}$ for very long periods even under unfavorable conditions. Other methods can also be used, since both the type of the laser and the reference wavelength are widely selectable. This allows highly accurate spectral measurements at any wavelength where a reference is not available. The method is therefore largely independent of the wavelength to be measured.

For generating a scattered radiation spectrum with a maximum number of frequencies, preferably successive laser pulses with different frequencies are emitted and scattered. To determine the scattered radiation spectrum, up to 1,000 or more and for example up to 10,000 or even up to 100,000 laser pulses can be scattered during the measurement period, for example, per second, hour or day. In this way, rapid changes in the scattered radiation spectrum, for example caused by a wind gust, can be detected. In addition, the frequencies of the laser pulses can be changed in rapid succession and, for example, in any desired sequential order and readily measured using the spectrum analyzer.

It must be taken into account in atmospheric measurements that the concentration and the transmission of the atmosphere can change dramatically from pulse to pulse. Spectral measurements are thus possible only when the laser changes the wavelength in rapid succession from pulse to pulse in a suitable manner. In an ideal system, the entire spectrum must be measured repeatedly within the shortest possible time. It is especially important to approach widely spaced frequencies as quickly as possible from pulse to pulse. This is technically feasible with sufficient accuracy only in a limited manner. In the method described herein, the frequency of successive laser pulses can be easily shifted by several thousand MHz. It is sufficient to determine the precise frequency of each laser pulse with an accuracy of less than one MHz. Even when it is not possible in advance to emit the laser pulse with exactly the desired frequency, the scattered radiation spectrum can be determined in the data analysis almost exactly from the measured frequencies of the laser pulses.

For this purpose, a suitable mathematical procedure is needed that does not assume that individual frequencies can be generated exactly as desired. Instead of building a more precise laser, it is sufficient to develop more elaborate software, which significantly simplifies the requirements and the expense of the experiment. In the aforedescribed method, each laser pulse used to determine the scattered radiation spectrum has a frequency (and spectral characteristics) that are determined exactly, thereby greatly improving the quality and spectral resolution of the measurement.

The frequency of the laser pulses can be adjusted, for example, as a function of the quantity of detected scattered radiation from already scattered laser pulses. If the detected scattered radiation does not yet include all parts of the spectrum that should be considered, then the frequency of the laser pulses can be at least coarsely shifted in the frequency ranges that have not yet been considered or were not sufficiently considered. At the beginning of the method according to the invention and at least during the initial commissioning of the device according to the invention, a laser pulse with an arbitrary frequency can be scattered initially. The quantity of scattered radiation caused by this laser pulse in combination with the determined frequency of the laser pulse can give an indication of frequency ranges that are of interest for the measurement. If necessary, several laser pulses with possibly very different frequencies may be required in order to obtain enough information for locating the frequency range. If the frequency range of interest, where for example a lot of scattered radiation is received, is known, then the frequency of the laser pulses can be shifted to this frequency range.

The absolute frequency of each laser pulse is determined only at the time of the data analysis by a comparison with the theoretical model. In particular, the atmosphere moves downward or upward by only mm/s on average. In a very good approximation, no Doppler shift occurs on average over a longer period and a larger altitude range, e.g. in the mesosphere, when precise vertical measurements are performed. This method for determining the absolute wavelength is more accurate than the use of a reference gas in a laboratory reference cell. The spectrum to be measured serves quasi itself as a reference cell. When the absolute frequency has been determined once, the additional reference laser is sufficient. The absolute frequency must be determined only once, as long as the spectrum analyzer is not mechanically modified and can also be performed by using a laboratory reference.

Absolute frequencies of the spectrum of the scattered radiation can be determined from their particular quantity distribution with respect to the at least one determined characteristic of the laser pulses. Specifically, the quantity (or amount) of the received scattered radiation can be linked to the exactly determined frequencies of the laser pulses and the generated scattered radiation spectrum can be compared with a theoretical model for translating the relative frequencies into absolute frequencies.

For determining properties of the gas, it may be necessary to know the absolute frequency values of the spectra of the backscattered radiation of the laser pulses. In order to determine at least one frequency of scattered radiation from the laser pulses used to determine the properties of the gas, the gas may be vertically illuminated and the backscattered radiation may be measured. Since the atmosphere moves on average up and down either not at all or only slowly, for example with a few millimeters per second, the Doppler shift of the backscattered portion can be neglected or can be averaged out under sufficiently long illumination. This method for determining at least one absolute frequency value of a laser, wherein a gas in the atmosphere is illuminated vertically and, for example, over a long period of time of up to one hour or up to 2, 4, 8 or 16 hours, or up to one day or longer, and the absolute frequency value is determined from the backscattered radiation, is advantageous also independent of the method for determining the scattered radiation spectrum of the laser pulses.

To be able to measure the gas properties at a predetermined distance or height in the atmosphere, the propagation time of the laser pulse required for reaching the gas volume to be examined and the propagation time of the scattered radiation from the gas volume to be examined back to the radiation sensor can be used. For example, properties of gas volumes at an altitude of several thousand meters can be determined.

In particular for measurements in the atmosphere, the laser pulse passes through other volumes of the atmosphere on its way to the gas volume to be examined where the laser pulse is at least partially scattered. The scattered radiation produced between the pulsed laser and the gas volume to be examined can be used to determine gas properties of additional gas volumes scattering the laser pulse.

For example, a large gas volume may be divided into several smaller gas volumes that are arranged between the pulsed laser and the gas volume to be examined that is disposed farthest from the pulsed laser The gas volumes which are, for example, arranged successively in a straight line may each generate a portion of the scattered radiation, wherein the backscattered portions of the laser pulse relating to each of the volumes are assigned to a distance channel in the device. The total gas volume to be examined may have many thousands and for example 8,000 distance channels with a distance resolution of a few millimeters, up to hundreds or even thousands of meters. When the measurement is carried out substantially vertically, the distance corresponds to the height.

Measurement data are generated when determining the scattered radiation spectra, for example, the backscattered intensity and the number of backscattered photons per height channel and laser pulse and the data related to the characteristics of the laser pulses, for example, the frequency, the energy and the quality of the laser pulses. One terabyte or even more of measurement data are generated each day when measurements are performed. Even if data for laser pulses, whose quality does not meet the quality criteria, and data for their scattered radiation are not stored, the amount of data is so large that the storage of data can no longer be handled quickly in a continuous operation of the device even when using of modern data storage devices. However, conventional compression methods are unable to significant or even highly compress the measurement data because the data have no structure, although the distribution of the measurement data is typically known.

It is therefore also the object of the invention to provide a method for compressing unstructured data, for example data corresponding to white noise and having a well-known distribution, in particular count data, with the method significantly compressing the data.

This object is attained by a method for compressing unstructured data with a known distribution, wherein a dataset of the data includes at least one source data field, a plurality of address data fields and for each address data field a target data field linked with one of the address data fields.

The unstructured data are in particular measurement data produced by the method according to the invention and the device according to the invention for determining the spectrum of scattered radiation. For example, the frequency of one of the laser pulses is entered in the source data field. Additional source data fields may include, for example, the intensity or the quality feature of this laser pulse. Channels, in particular height channels, may be assigned to the address data fields, wherein a scattered radiation spectrum should be determined for each height channel. The data set may have, for example, up to 8000 or more address data fields, so that scattered radiation spectra of, for example, 8000 height channels can be determined. A height channel represents for example a distance of 25 m, wherein 8,000 sequentially arranged height channels correspond to a measurement distance of 200 km. In particular, the quantity of backscattered radiation is stored in the target data field, wherein a quantity of scattered radiation associated with the height channels or the address data is stored in the target data field. The target data are in particular count data, i.e. natural numbers, and preferably the number of photons of the scattered radiation received per laser pulse and height channel.

To compress the data, the most frequently occurring target data and the address data associated therewith are not stored. A presence of source data without address data and target data represents here the most frequently occurring target data value.

To further reduce the storage requirements, target data values that occur less frequently and in particular with the second highest frequency, may not be stored and may be associated with the address data represented by them.

To also reduce the storage requirements for the address data, the address data may be converted into distance data, wherein the distance data include the distance and in particular the number of height channels in relation to a previous address data field, which includes for example address data values for target data values which occur less frequently than the most frequently occurring target data values. Thus, for example, instead of the value 3426 for the corresponding height channel, only the value 5 for the distance to the previous height channel 3421 with target data that occur less frequently than the most frequently occurring target data must be stored.

To be able to store not only the target data occurring with the second highest frequency, but also target data occurring even less frequently, a selected and for example minimum distance data value may represent an increase of the target data value associated with an address data field by a predetermined increment. For example, the minimum distance data value may correspond to the value zero and the predetermined increment may have the value one.

To keep the data word length of the distance data values as short as possible, a selected and for example maximum distance data value may represent an increase of the address data value without representation of a target data value. If the data word length of the distance data field is, for example, 4 bit, then the maximum distance data value may be represented by the value 15 (1111). If a corresponding distance data value is entered in the distance data field, then the most frequently occurring target data value is associated with following fourteen distance data fields. Only the address data value in the following fifteenth address data field can then represent a target data value that occurs less frequently than the most frequently occurring target data value. However, if no such target data value is associated with this address data field, then the address data value in the following fifteenth address data field can represent a value between 1 and 14 which indicates that one of the first to fourteenth address data field following this address data field represents for example the second-most frequently occurring target data value. Alternatively, the value 15 (1111) can again be stored instead of a value—between 1 and 14, which increments the distance value counter by 15 without increasing or representing target data values. If the second-most frequently occurring target data value is associated with the fifteenth address data field, then the target data value of null is preferably associated therewith.

By using the method of the invention, a terabyte of count data can be compressed into, for example, 10 gigabytes. The compression is hereby lossless.

This method is effective in particular for count data having a low count rate and a known distribution. The distribution may, for example, be a Poisson distribution and the count rate may be between 0 and 20.

The count data generated in the process of determining the scattered radiation spectrum correspond to the number of backscattered photons per pulse and height channel. In most situations, in particular for measurements at high altitudes of the atmosphere and for example in the mesosphere, no photon is backscattered to the device. The most frequently measured data value is therefore 0.

The second-most frequently occurring value corresponds for example to a single backscattered photon per laser pulse and height channel. Third-most frequently, for example, two photons are backscattered, wherein this value occurs very rarely.

The greater the height resolution is, the lower is the expected count rate. For a particularly high resolution, for example, a gas volume with a particularly small thickness is considered. This smaller gas volume scatters fewer photons compared to larger, i.e. thicker, gas volume, so that the count rate is equal to 0 rather than greater than 2. Consequently, the compression becomes more effective with improved height resolution.

The scattered radiation spectrum cannot be readily produced directly from the data obtained with the method according to the invention for determining the scattered radiation spectrum. To be able to obtain the scattered radiation spectrum by using the laser pulses, the invention moreover provides a method for calculating a scattered radiation spectrum, wherein frequencies of laser radiation to be scattered are linked with the amount of backscattered radiation, wherein frequencies of the laser radiation to be scattered associated with frequency intervals and quantities of determined scattered radiation associated with the frequencies are combined into respective frequency values and quantity values, wherein the frequency values and the quantity values are determined so that they approach as closely as possible values of an expected theoretical spectrum.

The frequency values and quantity values can be calculated by using various mathematical methods known in the art. For example, the frequency values and quantity values can be approximated to the expected theoretical scattered radiation spectrum by a compensation calculation. In the simplest case, a linear approximation may suffice. If the results of the linear approximation are not close enough to the expected theoretical scattered radiation spectra, then a higher-order approximation may be used. Furthermore, the frequencies or frequency ranges, wherein a larger quantity of scattered radiation was received and/or the quantities of scattered radiation associated with these frequencies or frequency ranges, can be weighted more heavily than frequencies or the quantities of scattered radiation associated with these frequencies or frequency ranges, where a lesser quantity of scattered radiation is received.

With the method according to the invention and the device according to the invention, scattering spectra of any kind can be readily and exactly determined by using available pulsed laser. The laser pulses can be scattered not only by a gas, in particular air, but also by other materials to determine a property of these materials, and the resulting scattered spectrum can be accurately determined.

Due to the achieved accuracy of the measurement method, not only highly accurate measurements can be performed, but characteristics of measuring instruments can be determined and physical theories can be reviewed. Discrepancies between theory and measurement show theoretical or instrument-related problems or other unknown factors, such as atmospheric conditions. This is achieved by the extremely accurate determination of the scattered radiation spectrum with a plurality of laser pulses whose frequencies were measured accurately. For example, the average spectral line shape or the average spectral width of the pulsed laser (typically Lorenz) can be determined with high accuracy from the flanks of the measured atmospheric spectra. Similarly, with an asymmetric line shape, the mirror spacing of the spectrum analyzer can be determined from the measurement. The measurement can also be used to verify the theory in addition to instrumental parameters. Any deviation of the observed spectrum is either due to an error in the system, insufficient consideration of the atmospheric conditions or an error in the model of the spectral line (including common software errors). A careful analysis of the measured data can uncover both experimental and theoretical problems.

The invention will now be explained based on exemplary embodiments and with reference to the drawings. The different features of the embodiments can be combined independently of one another, as has already been described for the individual advantageous embodiments.

Figure 2:
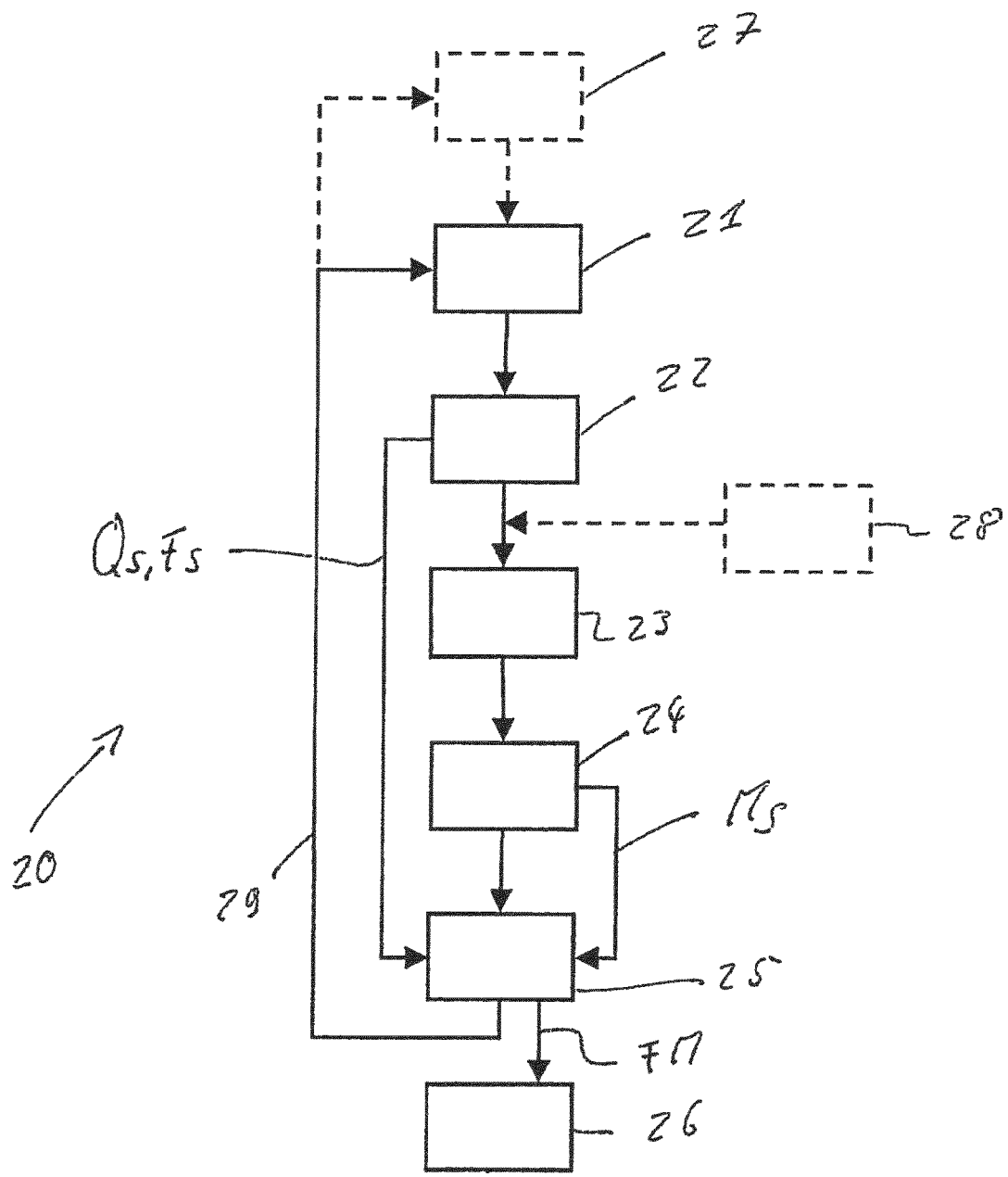
Figure 3:
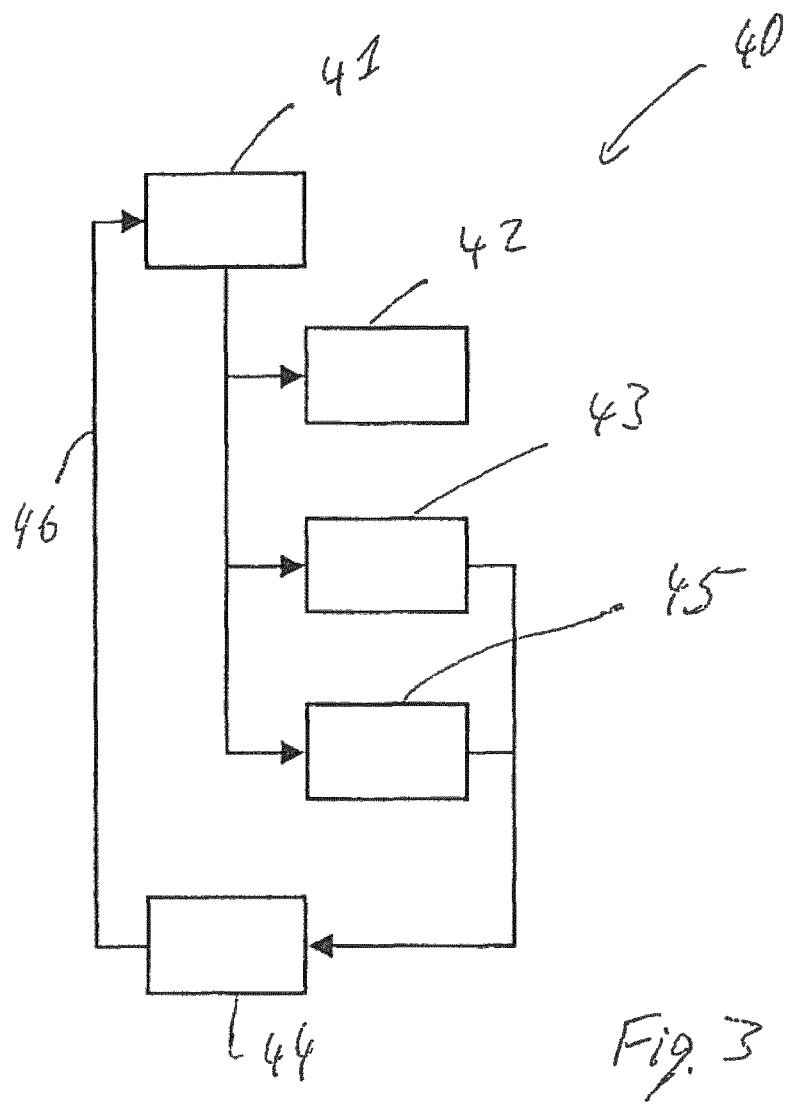
Figure 4:
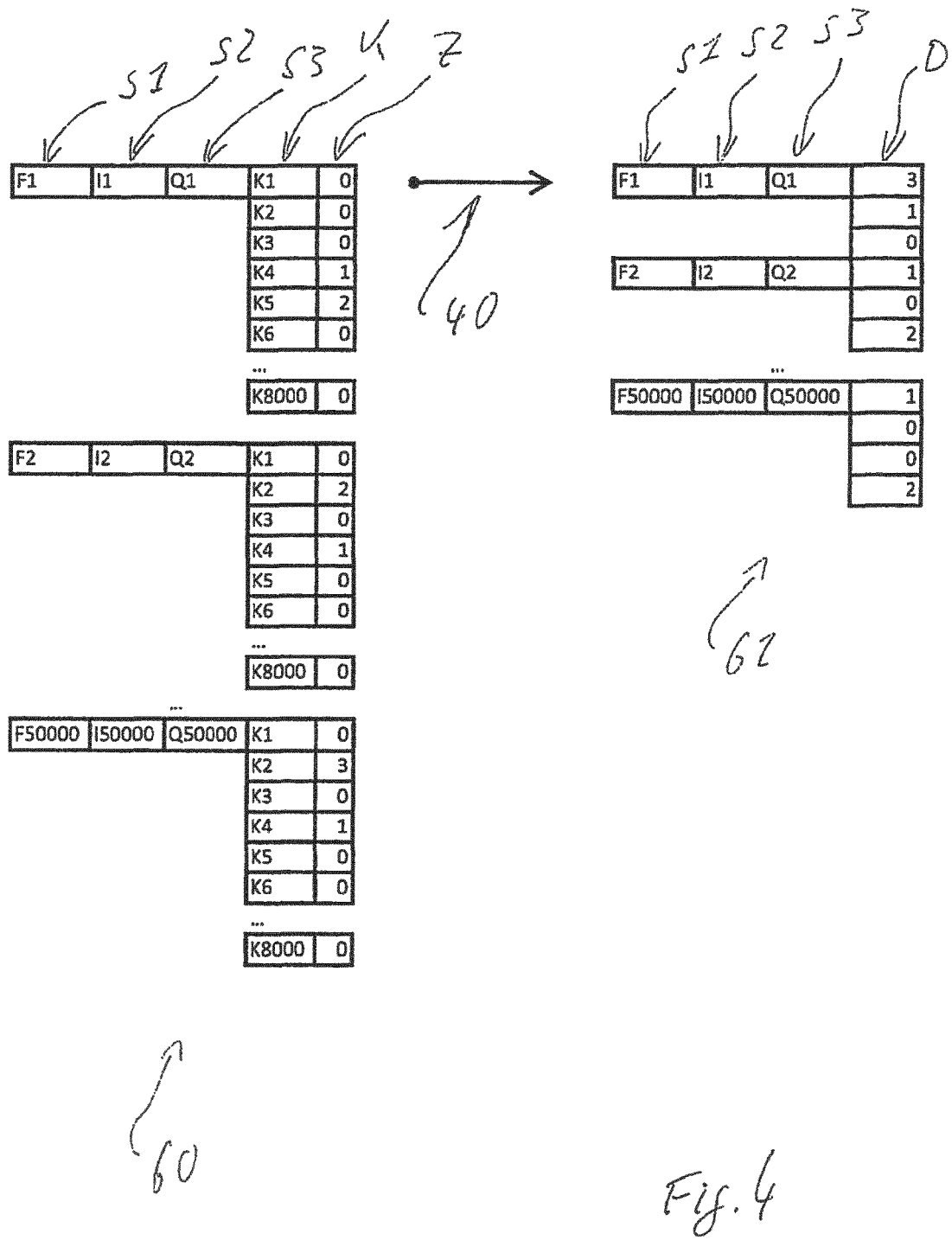
Figure 5:
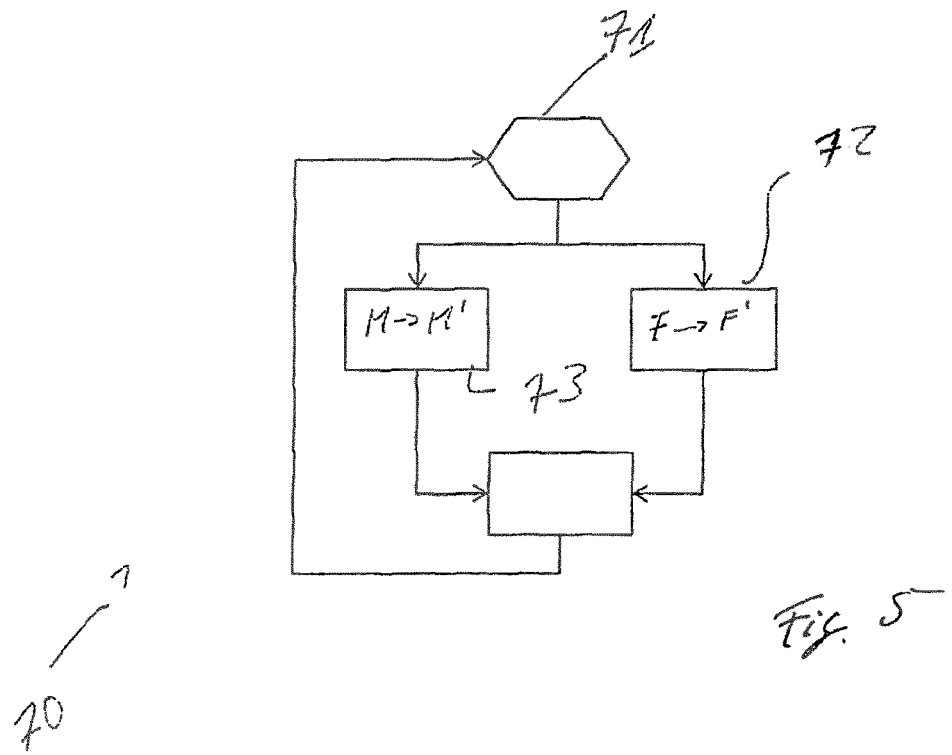
Figure 6:
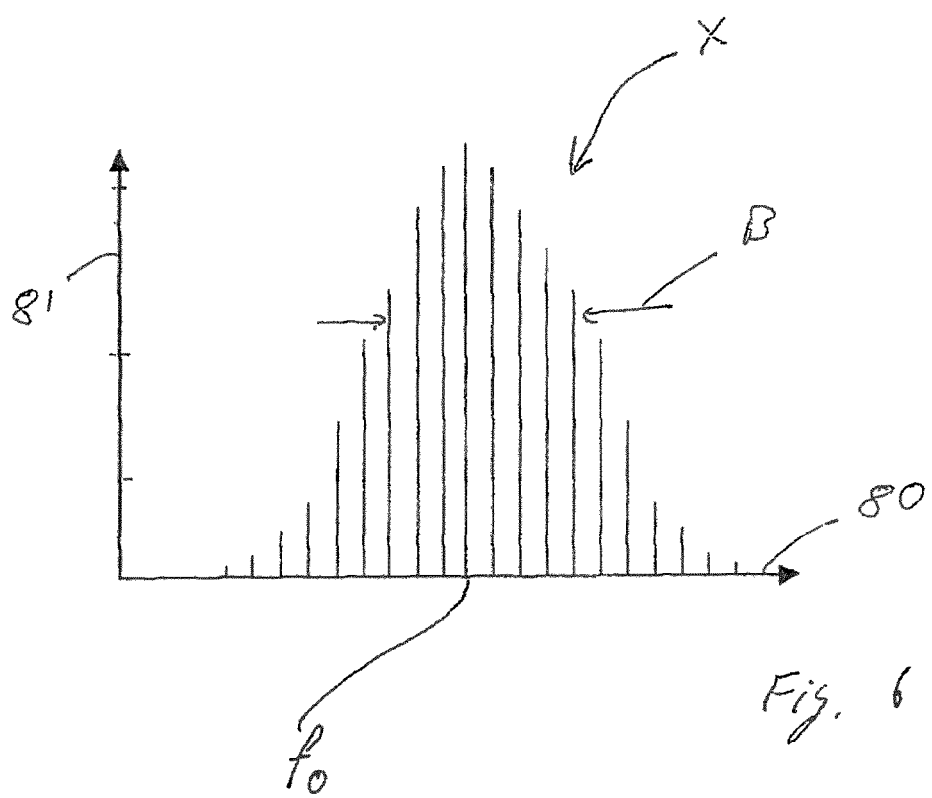

It is shown in:

FIG. 1 a schematic diagram of an exemplary embodiment of a device according to the present invention for determining a scattered radiation spectrum;

FIG. 2 a schematic diagram of an exemplary embodiment of a method according to the present invention for determining a scattered radiation spectrum in form of a flow diagram;

FIG. 3 a schematic diagram of an exemplary embodiment of a method according to the present invention for data compression in form of a flow diagram;

FIG. 4 a schematic diagram of data;

FIG. 5 a schematic diagram of an exemplary embodiment of a method according to the present invention for calculating a scattered radiation spectrum in form of a flow diagram; and FIG. 6 a schematic diagram of a scattered radiation spectrum.

The structure and function of a device according to the invention for determining a scattered radiation spectrum will be described first with reference to the exemplary embodiment of FIG. 1.

FIG. 1 shows schematically the device 1 for determining a scattered radiation spectrum with a pulsed laser 2 and a radiation sensor 3. The pulsed laser 2 is constructed to emit laser pulses P, wherein the emitted laser pulses P are scattered and scattered radiation S from the scattered laser pulses P is at least partially received by the radiation sensor 3. The laser pulses P are directed, for example, to a gas volume V in order to derive from the scattered radiation S at least one property of the gas volume V. Alternatively, the laser pulses P can also be directed to another volume, for example a volume of a liquid, or other structures for determining at least one property of these volumes or structures and can be scattered by these volumes or structures.

The laser pulse P emitted from the pulsed laser 2 propagates along an optical axis O2 in the direction of the gas volume V to be examined. A beam splitter 4, on which the laser pulse P is incident and by which the laser pulse P is scattered, is disposed along the optical axis O2 between the pulsed laser 2 and the gas volume V. A first portion P' of the laser pulse P exits the beam splitter 4 towards the gas volume V, where it is scattered. A second portion P''' of the laser pulse P is guided by the beam splitter 4 along an optical axis O4 of the beam splitter 4 to a spectrum analyzer 5. At least one characteristic of the laser pulse P can be determined with the spectrum analyzer 5 based on the second portion P'''. This characteristic is, for example, a selected frequency F of the laser pulse P and, in particular, the frequency F, where a frequency spectrum of the laser pulse P has its maximum or its center of gravity. Furthermore, a quality feature Q of the laser pulse P can be determined with the spectrum analyzer 5. The quality feature Q may include, for example, characteristics of laser modes or broadband emissions of the pulsed laser 2.

The spectrum analyzer 5 includes, for example, a laser radiation and in particular the second portion P''' of the laser pulse P with an interferometer superimposed on itself, a measurement signal converter, and a lens. The lens is preferably a convex lens arranged between the interferometer and the measurement signal converter in an optical path of laser light exiting the interferometer and guided to the measurement signal converter. The convex lens images onto the measurement signal converter an interference pattern of the laser radiation that is superimposed on itself.

The measurement signal converter generates a frequency signal Fs and/or a quality signal Qs, which can be outputted by the spectrum analyzer 5 to a computing unit 6 of the device 1. The computing unit 6 compares, for example, the quality signal Qs with a quality criterion. If the laser pulse P does not satisfy the quality criterion, then the data of the laser pulse P and its scattered radiation S are not considered in the determination of the scattered radiation spectrum and are for example discarded. If the laser pulse P satisfies the quality criterion, then its frequency F represented by the frequency signal Fs is at least temporarily stored in the computing unit 6. The computing unit 6 is also connected with the radiation sensor 3 for receiving the measurement signal. The radiation sensor 3 is in the exemplary embodiment of FIG. 1 configured to generate as a measurement signal a quantity signal Ms representative of the quantity (amount) M of received scattered radiation S and to transmit this signal to the computing unit 6. In the computing unit 6, at least the frequency F of the laser pulse P and the quantity M of the received scattered radiation S are linked together and outputted, for example as a data packet FM, to a storage device 8.

The computing unit 6 can determine, based on the quantity signal MS representative of the quantity M of scattered radiation S received by the radiation sensor 3 in combination with the frequency signal Fs representative of the frequency F of the laser pulse P, whether the frequency F of the laser pulses P generated by the pulsed laser 2 should be changed. For this purpose, a decision rule may be stored in the computing unit 6. The computing unit 6 can be connected with the pulsed laser 2 via a control line 8 for transmitting control signals and thereby affect the frequency F of the laser pulses P generated by the pulsed laser 2. If the pulsed lasers 2 is excited by a seeder laser 9 (shown by dashed lines), then the control line 8 may also be routed as a control line 8' (shown by dashed lines) from the computing unit 6 to the seeder laser 9, so that the computing unit 6 influences the frequency of the excitation radiation A of the seeder laser 9 that excites the laser pulses P.

The frequency F of the laser pulses P cannot readily be determined absolutely with the spectrum analyzer 5, but only relatively. If the spectrum analyzer 5 changes over time, for example due to temperature changes, then the frequencies F of the laser pulses P cannot be repeatedly accurately measured. In order to recognize a change of the spectrum analyzer 5, the device 1 may include a reference laser 10. The reference laser 10 emits during the operation of the device 1 reference radiation R with a reference frequency Fr to the spectrum analyzer 5. The reference frequency Fr was previously determined with the spectrum analyzer 5 at least once under controlled conditions. Since the reference frequency Fr is stable even over longer periods of time, changes of the spectrum analyzer 5 can be determined by re-measuring the reference frequency Fr. If the determined reference frequency Fr deviates too much from a previously determined reference frequency Fr, then this indicates a change in the spectrum analyzer 5. The reference frequency Fr needs thereby not be absolutely known. Measurements of the frequencies F of the laser pulses P can even be corrected based on the measurements of the reference frequency Fr performed at different times and on measurements producing mutually different measurement results.

In order to determine longer-term changes in the spectrum analyzer 5, it is sufficient to determine the reference frequency Fr with the spectrum analyzer 5 occasionally, for example every hour. In order to identify also short-term changes of the spectrum analyzer 5, the reference frequency Fr can be determined with the spectrum analyzer 5, for example, between two laser pulses P. Preferably, the reference frequency Fr is measured between all laser pulses P.

As an alternative to coupling the second portion P''' out of the laser pulse P into the beam splitter 4, the spectrum analyzer 5 can also be connected directly with the pulsed lasers 2. A portion of the laser pulses P may enter directly from the pulsed laser 2 into the spectrum analyzer 5, where the frequency F or the quality feature Q of the laser pulses P can then be determined. Such a spectrum analyzer is illustrated in the exemplary embodiment of FIG. 5 by dashed lines and provided with the reference numeral 5'.

The gas volume V is, for example, a gas volume in the upper atmosphere, and in particular in the mesosphere. In order to be able to determine properties of a gas at a low pressure, the gas should be irradiated with many laser pulses P. In particular, when the gas volume V is located in the upper atmosphere and, for example, in the mesosphere, at best only a few photons of scattered radiation S per laser pulse P reach the radiation sensor 3. However, the scattered radiation spectrum can nevertheless be determined due to the large number of employed laser pulses P. To determine the gas properties, the gas must be irradiated with laser pulses P of different frequencies F, so that laser pulses P of different frequencies F are consequently also scattered.

FIG. 2 shows a first exemplary embodiment of a method according to the invention. The same reference numerals are used for elements that correspond in function and/or structure to the elements of the exemplary embodiment of FIG. 1.

The method 20 for determining a spectrum of scattered radiation is shown schematically in FIG. 2 in form of a flowchart. In a first method step 21, a laser pulse P is emitted. In the following step 22, the frequency F of the laser pulse P is determined.

The laser pulse P, or at least the first portion P' of the laser pulse P, is scattered in method step 23 and the quantity M of generated scattered radiation S and received by the radiation sensor 3 is determined in method step 24. In a subsequent method step 25, the frequency F determined in method step 22 and the quantity M of scattered radiation S measured in step 25 are linked with one another. For this purpose, for example the frequency signal Fs and the quantity signal Ms are used. The frequency F associated with the quantity M is stored as a data packet FM in method step 26.

Before or after method step 21 and in particular between method steps 22 and 23, a reference frequency Fr can be measured in optional process steps 27, 28 in order to detect changes in the frequency measurement.

As indicated by the arrow 29, the method 20 may be executed repeatedly and for example up to 1000 times per second, up to 10,000 times per second or even up to 100,000 times per second or even more frequently. The frequency F of the laser pulse P can be changed in each pass of the method 20, in order to determine the scattered radiation spectrum with the largest possible number and/or widely spaced frequencies F.

In method step 22, the quality feature Q of the laser pulse P can also be determined and the signal Qs representing the quality feature Q can be outputted and used in method step 25. If the quality feature Q of the laser pulse P does not correspond to a quality criterion, then neither the frequency F of the laser pulse P nor the quantity M of received scattered radiation S is stored in method step 26.

The method 20 of the exemplary embodiment of FIG. 2 thus generates a large amount of data, for example, one terabyte for each day of measurements. Even modern data storage devices are unable to handle this amount of data generated every day when the measurements are performed daily. Conventional compression method for data are incapable of compressing the data generated by the method 20, since these data have little or no structure, i.e. their structure corresponds to white noise.

In particular, quantity data, i.e. count data, are generated when determining properties of gases in the upper atmosphere that correspond to the number of backscattered photons per laser pulse P. The expected distribution of the quantity M and the number of backscattered photons is known. For example, no photon is received by the radiation sensor 3 for many or even for most of the laser pulses P. As the second-most frequent event, a single photon is received. As the third-most frequent event, two scattered photons are received. Three or more scattered photons are received only in exceptional cases.

Because of the lack of data structures, these quantity data or count data can be compressed by conventional methods only poorly or not at all, because known compression methods compress data based on repetitive structures which, however, the measurement data lack. In particular, conventional compression methods are often incapable of significantly compressing the measurement data loss-free. In a lossy compression, however, the scattered radiation spectrum might be so greatly distorted that it cannot be determined.

FIG. 3 shows schematically a compression method 40, with the unstructured count data having a structure that corresponds to for example white noise, but has a known distribution, for loss-free compression. The compression method 40 is shown highly schematically in FIG. 3 as a flowchart.

In a first method step 41, count data is generated and, for example, the number or the quantity M of backscattered photons of a laser pulse P are counted in a channel, i.e. a gas volume with a predetermined thickness. When the laser pulses P are scattered by a gas volume V in the upper atmosphere, for example in the mesosphere, then most frequently zero photons, less frequently a single photon, even more rarely two photons and only in exceptional cases three or more photons per laser pulse P and height channel are received and counted. In method step 42 following method step 41, it is checked whether no photon at all was counted. If no photon is received by the radiation sensor 3 and if this is the most frequent event, then it is decided in method step 42 not to store at least the measured number of zero photons and possibly also not the data for the height channel as data, but to instead discard these data.

In method step 43, it is checked whether for example exactly one scattered photon has been received by the radiation sensor 3 as the second-most frequent result. For example, if just for one photon was received for one of the channels, then these data representative of a measurement, e.g. the number of height channels, are stored in method step 44. In particular, the distance to the height channel, where the same number of photons was previously received, is stored.

When exactly two photons were received, it is decided in method step 45 to store data for this measurement. However, it is not necessary to store the value two. To save memory space, it is sufficient to store the distance zero.

Because larger data sets with count data must usually be compressed, the compression method 40 is carried out repeatedly, as indicated by the arrow 46.

FIG. 4 shows schematically uncompressed data 60 and compressed data 61. The same reference numerals are used for elements corresponding in function and/or structure to the elements of the exemplary embodiments of the previous figures.

The uncompressed data 60, and the compressed data 61 include at least one source data field S1 and, for example, three source data fields S1, S2, S3, wherein source data can be stored. Source data are, for example, data of a first laser pulse P and, in particular, its determined frequency F1, its intensity I1, and possibly its quality Q1. Several address data fields K are associated with the at least one source data field S1. The number of address data fields K may correspond to the number of height channels and one address in the address field may be assigned to each of the height channels. In the illustrated exemplary embodiment, the uncompressed data 60 include address data fields K1 to K8000 for one of the laser pulses P 8000. The address data fields have a minimum length of 13 bits to allow the digital display of 8000 different address data values.

A target data field Z, where the quantity M of scattered radiation S for the associated height channel is registered for one of the scattered laser pulses P, is assigned to each of the address data fields K. In the illustrated exemplary embodiment, the most-frequent target data value is zero. This means that zero photons are received from the scattered laser pulse P for each channel. On the other hand, instead of zero photons, one photon or two photons were received for the respective address data K4 and K5.

The uncompressed data 60 furthermore include data for more scattered laser pulses P. For example, the uncompressed data 60 include data for 50,000 laser pulses P.

The compressed data 61 have, instead of the address data K1 to K8000 and the target data, only distance data D to a first data field or to a previous field that does not include the most frequently occurring target data value zero. For example, the target data value of one photon for the address data field K containing the address data K4 is represented by the distance data value three, which indicates that a target data value corresponding to the second-most frequent target data and for example the value of one photon exists only in the address data field K1 having a distance of three address data. The value of one following the value of three in the next field expresses that a target data value deviating from the most-frequent target data is contained already in the next target data field associated with the address data field K. However, the encoded target data does not match the value of one photon, but the value of two photons. To be able to encode the target data value of two photons, the smallest possible distance data value null follows the distance data value one. The smallest possible distance data indicates that the target data value needs to be incremented, e.g. by the value of one.

The compressed data 61 for the remaining laser pulses two to 50,000 are comparably encoded and compressed in this way.

FIG. 5 shows schematically a method 70 for determining the scattered radiation spectrum in form of a flowchart. The same reference numerals are used for elements corresponding in function and/or structure to the elements of the exemplary embodiments of the previous figures.

The method 70 uses the data generated with the device 1 or with the method 20 for determining the scattered radiation spectrum. The data represent discrete support points, which however cannot be readily assembled into the scattered radiation spectrum. The method 70 starts at a first method step 71. In method step 71, the method 20 is for example repeatedly performed to determine frequencies of F of scattered laser pulses P and quantities M of backscattered radiation S. A plurality of frequencies F and quantities M are forwarded to method steps 72 and 73 that follow the first method step 71. Frequencies F located within a frequency interval are combined in method step 72 to a combined frequency value F'. In method step 73, quantities M of scattered radiation S associated with the frequencies F of the frequency interval are combined to a combined quantity value M'.

The values of the combined frequency F' and the combined quantity M' are determined or calculated so that these values approximate as closely as possible expected values of a theoretical spectrum. For example, the combined frequency value F' and the combined quantity value M' can be calculated by a linear approximation or higher-order approximation and matched to the expected theoretical spectrum. Other calculation methods can also be used. For example, the frequencies F and the quantities M can be weighted based on the number of frequencies F in the frequency interval, or the intensity of the laser pulses P can be weighted with the frequencies F in the frequency interval. It may also be necessary to determine and store at least the relative intensity of the laser pulse P in addition to the frequency F.

If the frequencies F and the quantities M cannot be combined so that their combined values F', M' approximate closely enough values of the expected theoretical spectrum, then this may indicate a malfunction of the device 1 or a fault in the theoretical model.

FIG. 6 shows schematically a scattered radiation spectrum X determined with the device 1 and/or the method 20 and calculated with the method 70. The scattered radiation spectrum X is shown greatly simplified.

Values of the frequencies F of the laser pulses P are depicted on an x-axis 80 (abscissa). The values of the quantity M and the number of scattered photons measured by the radiation sensor 3 are depicted on the y-axis 81 (ordinate). The scattered radiation spectrum X of FIG. 6 shows combined quantity values M' only for twenty combined frequency values F of the laser pulses P. However, many thousands of combined frequency values F' and associated quantity values M' are often necessary for determining properties of the matter scattering the photons.

The spacings and/or widths of the frequency intervals may be different from the distances shown. A realistic scattered radiation spectrum X covering all possible variants cannot be readily represented graphically, so that only the twenty frequency values F' with the associated quantity values M' are shown in the illustrated exemplary embodiment for clarity.

The scattered radiation spectrum X has a maximum at a frequency f0. For example, many thousands or even millions of photons are counted over a period of, say, 24 hours at this frequency f0. Laser pulses P with the frequency f0 or an at least similar frequency F were scattered multiple times to receive that many scattered photons. Laser pulses P with frequencies F deviating from the frequency f0 were perhaps emitted at a similar rate. However, fewer photons were backscattered, which is evident from a smaller number of quantity values M' or count rate for frequency values F' of such laser pulses P, as depicted on the axis 81.

An absolute frequency value can be assigned to the measured frequency f0 based on theoretical models. Furthermore, the scattered radiation spectrum X has a width B. The shape of the scattered radiation spectrum X can also be determined based on the measurement. The absolute value of the frequency f0, the width B of the scattered radiation spectrum X and the shape of the scattered radiation spectrum X allow conclusions about the properties of the matter scattering the laser pulses P. For example, the temperature of the gas scattering the laser pulses P in the mesosphere can be determined. Likewise, flow rates of gases in the mesosphere can be accurately determined to within 1 m/s or even 0.1 m/s. When suitable models are available, other properties of the matter scattering the laser pulses P can also be highly accurately determined with the method 20 according to the invention and the device 1 according to the invention.

LIST OF REFERENCE SYMBOLS

1 Device
2 Pulsed laser
3 Radiation sensor
4 Beam splitter
5, 5' Spectrum analyzer
6 Computing unit
8, 8' Storage device
9 Seeder laser
10 Reference laser
20 Method
21, 22, 23, 24 Method step
25, 26, 27, 28 Method step
29 Arrow
40 Compression method
41, 42 Method step
43, 44, 45 Method step
46 Arrow
60 Uncompressed data
61 Compressed data
70 Evaluation method
71 Start
72, 73 Combine
80 Abscissa
81 Ordinate
A Excitation radiation
B Width
D Distance data
F Frequency
F' Combined frequency value
FM Data packet
Fr Reference frequency
Fs Frequency signal
f0 Frequency
F1, I1, Q1 Source data
K Address data field
K1 . . . K8000 Address data
M Quantity
M' Aggregate quantity value
Ms Quantity signal
O2 Optical axis
O4 Optical axis of the beam splitter
P Laser pulse P' First portion of the laser pulse
P" Second portion of the laser pulse
Q Quality feature
Qs Quality signal
R Reference radiation
S Scattered radiation
S1, S2, S3 Source data field
V Gas volume
X Scattered radiation spectrum
Z Target data fields

The invention claimed is:

1. The method for determining a spectrum of scattered radiation, wherein several laser pulses are successively scattered, the method comprising the steps of:
   measuring the scattered radiations per height channel and per laser pulse;
   determining at least one characteristic of each laser pulse; and
   linking the at least one characteristic of each laser pulse with the scattered radiation per height channel and per laser pulse for determining the spectrum of scattered radiation;
   wherein the method comprises the step of determining the frequency of each laser pulse as the characteristic.

2. The method according to claim 1, further comprising: detecting a portion of the scattered radiation for each laser pulse; and
   linking the quantity of detected scattered radiation with the determined characteristic of the scattered laser pulse.

3. The method according to claim 1, further comprising: determining a quality feature of the laser pulses and
   using only those laser pulses and scattered radiation associated with those laser pulses to determine the spectrum whose quality feature satisfies a quality criterion.

4. The method according to claim 3, further comprising determining the spectrum of the laser pulses for determining the quality feature.

5. The method according to claim 1, further comprising determining a frequency of a reference beam before or after at least one of the laser pulses.

6. The method according to claim 5, further comprising determining the frequency of the reference beam between several of the laser pulses.

7. The method according to claim 1, further comprising scattering laser pulses having different frequencies in succession.

8. The method according to claim 7, further comprising setting the frequency of the laser pulses based on the quantity of the detected scattered radiation.

9. The method according to claim 1, further comprising determining absolute frequencies of the spectrum of the scattered radiation from their quantity distribution in relation to the at least one determined characteristic of the laser pulses.

10. A device for determining a spectrum of scattered radiation, comprising:
    a pulsed laser whose laser pulses emitted during operation of the device are scattered for generating the scattered radiation;
    a radiation sensor that is configured to at least partially receive the scattered radiation, and
    a spectrum analyzer which is connected with the pulsed laser for receiving laser radiation and which is further configured to determine a characteristic of the laser pulses;
    wherein the characteristic is the frequency of the laser pulses; and
    wherein the device comprises a computing unit that links the determined frequency of the laser pulses with the quantity of detected scattered radiation per height channel and per laser pulse.

11. The device according to claim 10, wherein the radiation sensor is configured to generate a quantity signal that is dependent on the quantity of the received scattered radiation.

12. The device according to claim 10, wherein the spectrum analyzer comprises an interferometer that superimposes incident laser light with itself, a measurement signal converter, and a lens, wherein the lens is arranged between the interferometer and the measurement signal converter in a beam path of laser light exiting from the interferometer and propagating to the measurement signal converter.

13. The device according to claim 10, further comprising a reference laser, wherein the spectrum analyzer is arranged in the beam path of the reference laser.

14. A method for calculating a scattered radiation spectrum, wherein frequencies of laser radiation to be scattered are linked with the quantity of backscattered radiation per height channel and per laser pulse, the method comprising the steps of:
    measuring frequencies of the scattered laser radiation associated with frequency intervals; and
    in each case combining quantities of scattered radiation associated with the measured frequencies into frequency values and quantity values;
    wherein the frequency values and quantity values are determined so as to approximate values of an expected theoretical spectrum.

* * * * *